United States Patent [19]
Tsuchita et al.

[11] Patent Number: 4,531,413
[45] Date of Patent: Jul. 30, 1985

[54] ULTRASONIC FLAW DETECTOR DRIVING APPARATUS OF A TRACKLESS TYPE

[75] Inventors: Kenji Tsuchita, Hitachiota; Kozo Domon, Hitachi; Fuminobu Takahashi, Katsuta, all of Japan

[73] Assignee: Hitachi, Ltd., Tokyo, Japan

[21] Appl. No.: 535,694

[22] Filed: Sep. 26, 1983

[30] Foreign Application Priority Data

Sep. 29, 1982 [JP] Japan .................. 57-170172

[51] Int. Cl.³ ............................................. G01N 29/04
[52] U.S. Cl. ........................................ 73/637; 73/638; 73/640
[58] Field of Search .................. 73/637, 638, 639, 640

[56] References Cited

U.S. PATENT DOCUMENTS

| | | | |
|---|---|---|---|
| 3,999,423 | 12/1976 | Tyree | 73/67.8 |
| 4,108,004 | 8/1978 | Murakami | 73/638 |
| 4,434,660 | 3/1984 | Michaels et al. | 73/637 |

FOREIGN PATENT DOCUMENTS

| | | |
|---|---|---|
| 83109687 | 12/1983 | European Pat. Off. . |
| 2753635 | 6/1978 | Fed. Rep. of Germany . |
| 2930628 | 7/1980 | Fed. Rep. of Germany . |
| 2933619 | 10/1980 | Fed. Rep. of Germany . |
| 52-53488 | 4/1977 | Japan . |
| 57-108753 | 7/1982 | Japan . |
| 55138652 | 10/1982 | Japan . |

*Primary Examiner*—Howard A. Birmiel
*Attorney, Agent, or Firm*—Antonelli, Terry & Wands

[57] ABSTRACT

An ultrasonic flaw detector driving apparatus with no guide rail and including a traveling member (2) capable of being freely mounted to and dismounted from piping (1) to be inspected, and a turning member (3) detachably attached to the traveling member for turning movement thereabout. The traveling member is equipped with a multiplicity of sets of traveling rolling elements (9,9a) maintained in contact with an outer peripheral surface of the piping and spaced apart from one another circumferentially of the piping while each set of the traveling rolling elements of comprises at least two rolling elements which are spaced apart from each other axially of the traveling member (2). The turning member (3) is equipped with at least one ultrasonic wave probe (4) which scans the outer peripheral surface of the piping to inspect it. As the traveling rolling elements (9,9a) are rotated, the traveling member (2) travels on the pipe axially thereof, and the turning member (3) moves in turning movement about the traveling member as it is driven, so that the ultrasonic wave probe can scan both axially and circumferentially of the piping to inspect the whole area of the outer peripheral surface of the piping.

9 Claims, 8 Drawing Figures

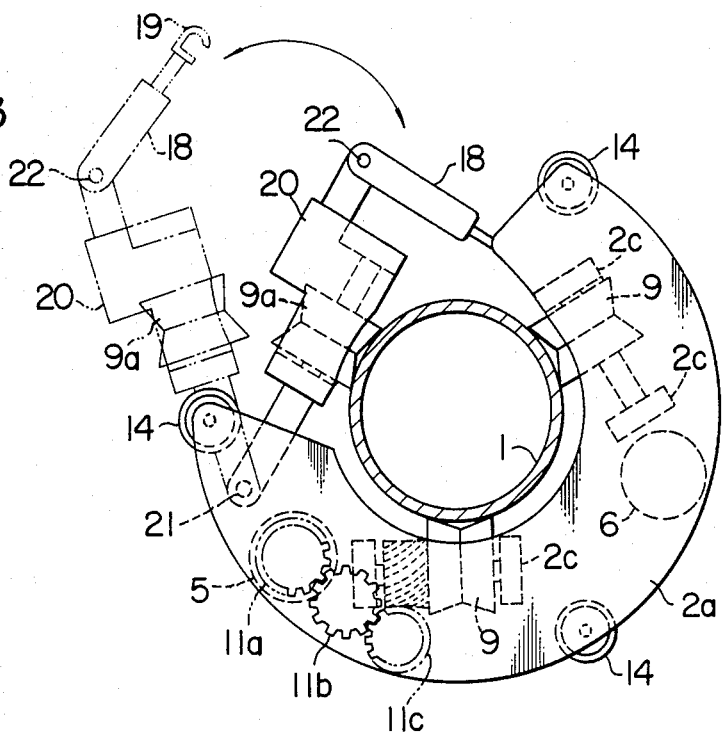
FIG. 3
FIG. 3A
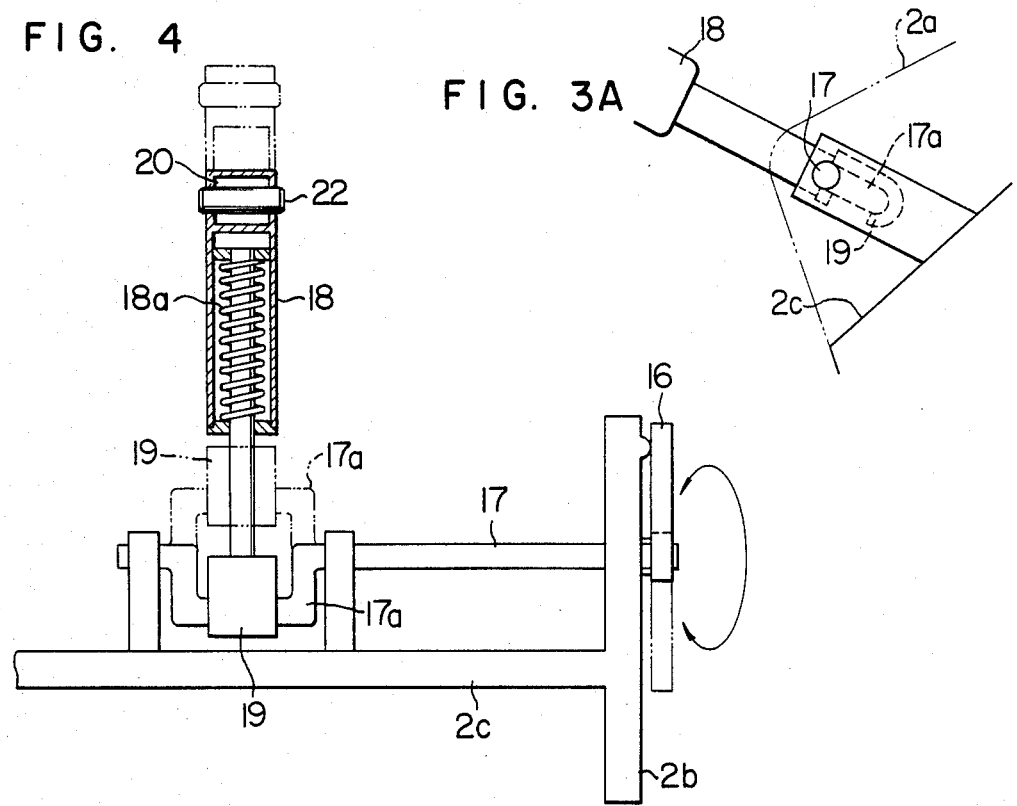
FIG. 4

ULTRASONIC FLAW DETECTOR DRIVING APPARATUS OF A TRACKLESS TYPE

FIELD OF THE INVENTION

This invention relates to ultrasonic flaw detector driving apparatus for piping, for example, and more particularly it is concerned with an ultrasonic flaw detector driving apparatus of the type described which has no guide rail for performing inspection of the piping by scanning an ultrasonic probe in both axial and circumferential directions on the piping.

DESCRIPTION OF THE PRIOR ART

FIG. 1 shows one example of the ultrasonic flaw detector driving apparatus of the prior art which has been proposed in Japanese Patent Laid-Open No. 18987/80 filed by the applicant of the subject application.

In the ultrasonic flaw detector driving apparatus of the prior art shown in FIG. 1, a frame A has a built-in motor fitted thereto which drives a pinion which in turn is maintained in meshing engagement with a rack C on a guide rail B, so as to move an ultrasonic wave probe D circumferentially of piping E (in the direction of an arrow Y) to scan the probe D in the circumferential direction to inspect the pipe E. The frame A has another built-in motor fitted thereto for moving arms F axially of the piping E (in the direction of an arrow X) to scan the probe D in the axial direction to inspect the pipe E.

The ultrasonic flaw detector driving apparatus outlined hereinabove being of a type having a guide rail, has some disadvantages. They include the following:

(1) The use of a guide rail places limitations on the zone in which the probe can scan. Thus, when the piping to be inspected is great in length, the guide rail should be attached to and detached from the piping a multiplicity of times, making inspection with the ultrasonic probe a time-consuming operation;

(2) Mounting and dismounting of the apparatus to and from the piping poser a problem when a portion of the piping to be inspected is located in a narrow area to which access can only be had with difficulty. Thus, the zone in which inspection can be performed is naturally restricted; and (3) An increase in the length of the arms would make it necessary to increase the rigidity of the apparatus as a whole, making it impossible to obtain an overall compact size and a light weight in an ultrasonic flaw detector driving apparatus.

SUMMARY OF THE INVENTION

A principal object of this invention is to provide an ultrasonic flaw detector driving apparatus which has particular utility for use in performing inspection of elongated piping in a short period of time with a high degree of efficiency.

Another object is to provide an ultrasonic flaw detector driving apparatus which has particular utility in carrying out inspection of a portion of the piping located in an area to which access can only be had with difficulty while being able to accomplish the aforesaid principal object.

Still another object is to provide an ultrasonic flaw detector driving apparatus which enables an overall compact size and a light weight to be obtained in an ultrasonic flaw detector driving apparatus while being able to accomplish the aforesaid other objects.

According to the invention, there is provided an ultrasonic flaw detector driving apparatus of a type having no guide rail enabling inspection of piping to be achieved, comprising a traveling member capable of being mounted to and dismounted from the piping, and a turning member detachably attached to the traveling member, wherein the traveling member is equipped with a multiplicity of sets of traveling rolling elements located in positions on an outer peripheral surface of the piping spaced apart from one another circumferentially of each set of piping while the traveling rolling elements includes at least two rolling elements which are in contact with the outer peripheral surface of the piping and spaced apart from each other axially of the piping so that as the traveling rolling elements are rotated the traveling member can travel axially of the piping on the outer peripheral surface thereof, and wherein the turning member is equipped with at least one ultrasonic wave probe for effecting scanning to perform inspection of the piping and capable of turning about the traveling member circumferentially of the piping.

Additional and other objects, features and advantages of the invention will become apparent from the following description when considered in conjunction with the accompanying drawings.

BRIEF DESCRIPTION OF THE DRAWINGS

FIG. 3 is a side view of the end plate portion of the embodiment of the ultrasonic flaw detector driving apparatus in conformity with the invention;

FIG. 3A is an enlarged view of an essential portion of FIG. 3;

FIG. 4 is a fragmentary view showing, in cross section, the retractile arm shown in FIG. 3 and parts associated with the retractile arm of the embodiment shown in FIG. 2;

DETAILED DESCRIPTION OF THE PREFERRED EMBODIMENTS

Figure 1:
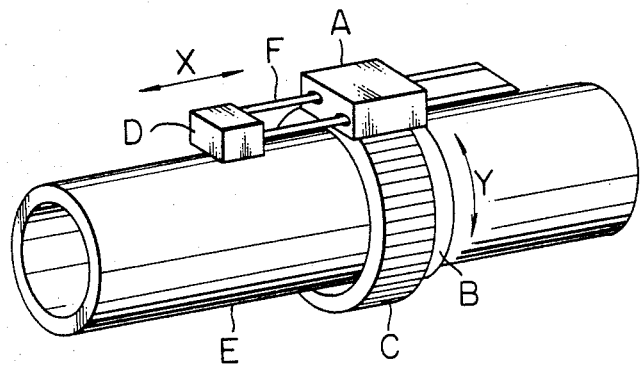
FIG. 1 is a perspective view of an ultrasonic flaw detector driving apparatus of the prior art arranged on piping.
Figure 2:
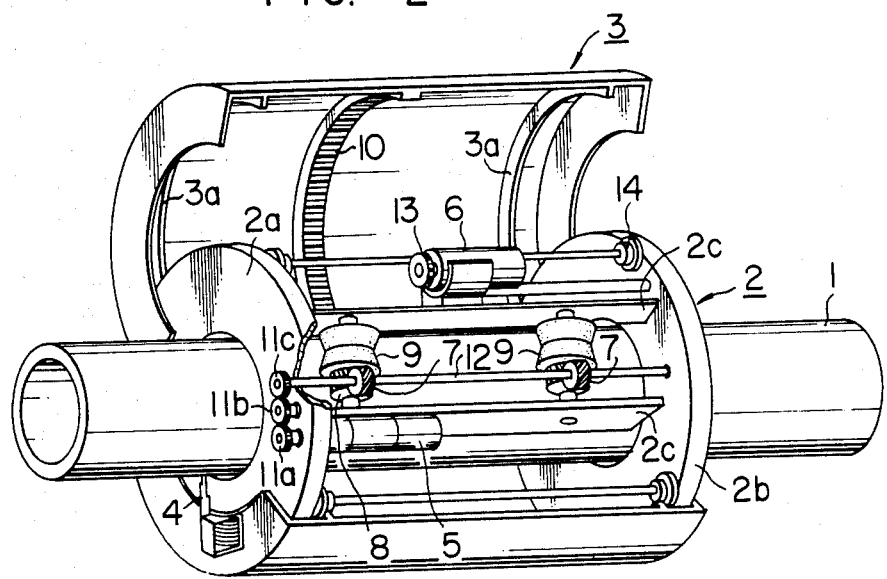
FIG. 2 is a perspective view of the ultrasonic flaw detector driving apparatus comprising one embodiment of the invention, showing the driving apparatus mounted to the piping while the turning member is disposed in an open position.

Referring to FIG. 2, one embodiment of the ultrasonic flaw detector driving apparatus in conformity with the invention comprises a traveling member 2 mounted to an outer peripheral surface of piping 1 to be inspected and movable axially thereof, and a turning member 3 detachably attached to the traveling member 2 for turning movement thereabout and equipped with an ultrasonic wave probe 4.

The traveling member 2 includes a main body composed of two end plates 2a and 2b each in the form of a disc having a cutout portion and formed with an opening which allows the piping 1 to extend therethrough, and a multiplicity of axially-oriented connectors 2c connecting the end plates 2a and 2b together to provide a unitary structure. A drive motor 5 fitted to one of the connectors 2c for driving the traveling member 2 drives worm gears 7 secured to a shaft 12 through gears 11a, 11b and 11c supported on the end plate 2a. The shaft 12 is journaled on the end plates 2a and 2b. Traveling rollers 9 each supported on a shaft and located perpendicular to the axis of the traveling member 2 between the adjacent two connectors 2c have a worm wheel 8 secured thereto coaxially therewith for meshing engagement with one of the worms 7, so that the traveling rollers 9 are driven for rotation by the motor 5. When the traveling member 2 is mounted to the outer peripheral surface of the piping 1, the traveling rollers 9 are brought into contact with the outer peripheral surface of the piping and perform the function of moving the traveling member 2 axially of the piping 1 as the drive motor 5 is actuated. The traveling rollers 9 each have a tread covered with a rubbery material to prevent a slip of the rollers 9 on the piping 1 from occurring. The two travelling rollers 9 spaced apart from each other axially of the traveling member 2 form a set, and a multiplicity of sets of traveling rollers 9 are provided to the traveling member 2 and arranged circumferentially thereof in spaced-apart relation. In the embodiment shown and described herein, the number of the sets of traveling rollers 9 is three.

Referring to FIG. 3, two sets of traveling rollers 9 of the three sets thereof are supported on the connectors 2c which are component parts of the main body of the traveling member 2, and each roller of the other set of travelling rollers 9a is supported by an arm 20 pivotally connected to a shaft 21 connected to the end plates 2a and 2b. Thus, the set of traveling rollers 9a supported by the arm 20 can be moved between a closed position shown by solid lines in which the traveling rollers 9a are in contact with the outer peripheral surface of the piping 1 and an open position shown by dotted lines in which the traveling rollers 9a are away from the outer peripheral surface of the piping 1, as the arm 20 is moved in pivotal movement. When they are in the solid line position, the three sets of traveling rollers 9, 9a are spaced apart equidistantly from one another circumferentially of the piping 1.

Referring to FIG. 3A and FIG. 4, one of the connectors 2c supports an eccentric shaft 17 which extends at one end portion thereof through the end plate 2b to provide an extension which has a handle 16 secured to its end. The eccentric shaft 17 has an eccentric portion 17a located midway between the end plates 2a and 2b, and a retractile arm 18 provided with a hook 19 at its forward end is connected through a shaft 22 to an end of the arm 20 which corresponds to the eccentric portion 17a of the eccentric shaft 17. The retractile arm 18 has a built-in spring 18a functioning to bias the arm 18 in a contracting direction. When it is desired to mount the traveling member 2 to the outer peripheral surface of the piping 1, the arm 20 and retractile arm 18 are first shifted to their open positions shown by phantom lines in FIG. 3 to allow the piping 1 to be inserted in the openings formed at the end plates 2a and 2b from one side by utilizing the cutout portions of the end plates 2a and 2b, and then the arm 20 and retractile arm 18 are pivotally moved in a clockwise direction in FIG. 3 to bring the eccentric portion of the eccentric shaft 17 to a phantom line position shown in FIG. 4 and hitch the hook 19 onto the eccentric portion. Thereafter, the handle 16 is allowed to make a substantially one-half revolution to bring the eccentric portion of the eccentric shaft 17 to a solid line position shown in FIG. 4. This operation allows the rollers 9a, arm 20 and retractile arm 18 to be resiliently clamped to their closed positions shown by solid lines in FIG. 3. The traveling rollers 9a are resiliently brought into contact with the outer peripheral surface of the piping 1 by the biasing force of the spring 18a. When it is desired to dismount the traveling member 2 from the piping 1, the end can be attained by performing the aforesaid process in reverse.

Attention is directed to the fact that various component parts of the traveling member 2 including the drive motor 5 for traveling, a turning member drive motor 6, the gears 11a–11c, a gear 13, single-flanged bearings 14, the handle 16, the eccentric shaft 17, the retractile arm 18 and the arm 20 are scatteredly arranged in such a manner that when the traveling member 2 is mounted to the piping 1, it is balanced in weight peripherally of the piping 1.

The turning member 3 turns about the traveling member 2 and is cylindrical in shape and composed of two semi-cylindrical portions, as shown in FIG. 2, which are hingedly connected together, although no hinges are shown. When the turning member 3 is fitted to the traveling member 2, an internal gear 10 on an inner surface of the turning member 3 is brought into meshing engagement with the pinion 13 of the turning member drive motor 6 supported on one of the connectors 2c, and ribs 3a attached to the inner surface of the timing member are fitted between the flanges of the two single-flanged bearings 14 supported by a shaft in the traveling member 2 and guided thereby, so as to thereby enable the turning member 3 to move in turning movement about the traveling member 2. Although not shown, the turning member 3 is equipped with clamp means for clamping the two semi-cylindrical portions thereof to each other to hold same in a unitary condition when the turning member 3 is fitted to the traveling member 2. The probe 4 for effecting scanning over the piping 1 is connected to one end face of the turning member 3. In FIG. 2, the probe 4 is shown as having one probe mounted on a left end face. However, the invention is not limited to this number and position of the probe and any desired number of probes may be fitted to either a left or right end face as desired.

In performing inspection of the piping to detect any flaw that might exist therein, the traveling member 2 is mounted to the piping 1 by following the process described hereinabove and then the turning member 3 is fitted to the traveling member 2, thereby making the ultrasonic flaw detector driving apparatus ready for operation. Then, upon actuation of the traveling member drive motor 5 and turning member drive motor 6, the traveling member 2 travels on the piping 1 in an axial direction while the turning member 3 moves in turning movement about the traveling member 2, so that the probe 4 fitted to the turning member 3 scans over the whole area of the outer peripheral surface of the piping 1 to carry out ultrasonic flaw detection. The ultrasonic flaw detector driving apparatus is not mounted to a guide rail but directly mounted to an outer peripheral surface of piping to be inspected with no guide rail thereon, so that it is possible to carry out inspection of the whole area of the outer peripheral surface of any elongated piping continuously without any interruption. The arrangement whereby the traveling member is balanced in weight peripherally of the piping and the sets of traveling rollers are equidistantly spaced apart from one another axially of the piping enables the traveling member to travel straightforwardly without moving in serpentine movement. This is conducive to increased accuracy and precision of scanning operations. Moreover, the arrangement whereby the use of a guide rail is eliminated and the drive section for the traveling member and the drive section for the turning member are located within the traveling member and scattered peripherally thereof enables an overall compact size to be obtained in a ultrasonic flaw detector driving apparatus and allows mounting and dismounting to be performed readily with a high degree of efficiency by following the simple process of bringing the hook into and out of engagement with the eccentric shaft, turning the handle, and opening and closing the turning member by fitting the ribs between the flanges of the single-flanged bearings and releasing them therefrom.

In the embodiment shown and described hereinabove, only one set of traveling rollers are driven by a motor. However, the invention is not limited to this specific manner of driving of the traveling rollers and other sets of traveling rollers may also be driven for movement by means of a motor or motors. In the embodiment, three sets of traveling rollers have been described as being used. However, this is not restrictive and any number of sets of rollers may be used so long as the number is two or more than two. The traveling rollers have been shown and described as each having a tread of a V-shape. However, the tread may be either flat or arcuate in shape that conforms to the shape of the outer peripheral surface of piping. The tread of each traveling roller has been described as being covered with a rubbery material. However, this is not restrictive and any other material may be used. Also, the traveling rollers themselves may be formed of a material of high coefficient of friction to avoid slipping thereof when brought into contact with the outer peripheral surface of piping, or a metal, such as magnetized metal, which enables the ultrasonic flaw detector driving apparatus to be magnetically or otherwise attracted to the piping may be used. Since the traveling rollers move in rolling movement and allow the traveling member to travel on the piping while they are maintained in frictional engagement with the piping, they may be replaced by other suitable members which can move in rolling movement while being maintained in frictional engagement with the piping, such as clawlers, without departing from the scope of the invention.

Figure 5:
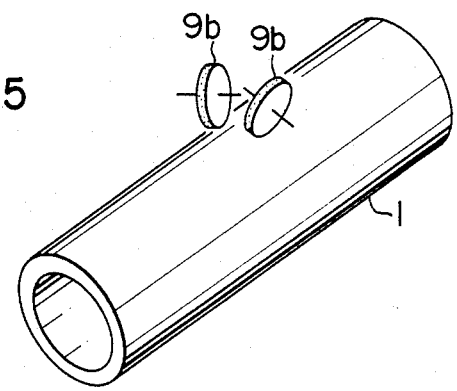
FIG. 5 is a perspective view of the traveling rollers representing a modification of the traveling rollers shown in FIG. 3, showing the traveling rollers arranged on the piping at a caster angle.
Figure 6:
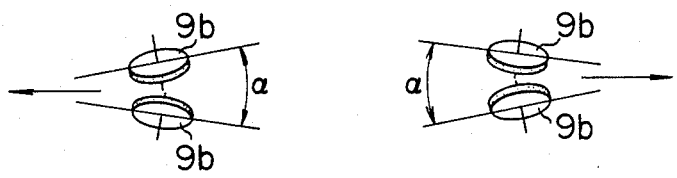
FIG. 6 is a perspective view of the traveling rollers representing another modification of the traveling rollers shown in FIG. 3, showing the traveling rollers for forward and backward movement arranged at a caster angle.

In order for the probe 4 to accurately and precisely scan over the outer peripheral surface of the piping 1, it is essential that the traveling member 2 travel straightforwardly without turning about the piping 1. This requirement can be satisfied admirably because a multiplicity of traveling rolling members are maintained in contact with the outer peripheral surface of the piping 1. In the present invention, in order to ensure that the traveling member 2 travels straightforwardly without fail, modifications of the traveling rollers shown in FIGS. 5 and 6 may be used. As shown, the traveling rollers are composed of two rollers 9b, 9b forming a set which are inclined at a predetermined caster angle α.

Figure 7:
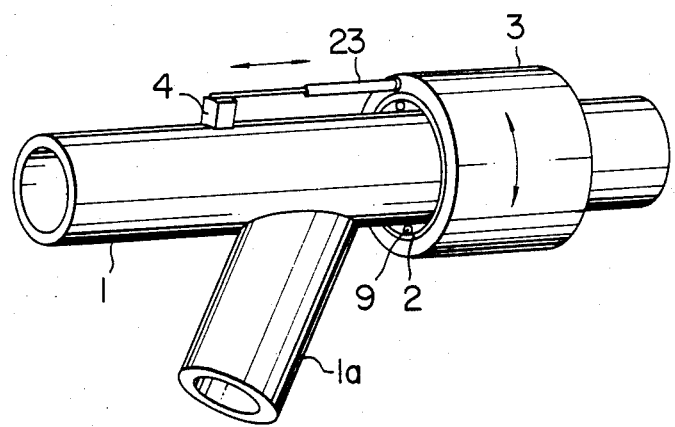
FIG. 7 is a perspective view of the ultrasonic flaw detector driving apparatus comprising another embodiment, showing the apparatus mounted to the piping.

FIG. 7 shows another embodiment of the invention in which the ultrasonic wave probe 4 is fitted to an end face of the turning member 3 through a retractile arm 23. Other parts of the embodiment are similar to those of the embodiment shown in Figs. 1-4. The embodiment shown in FIG. 7 has particular utility in performing inspection to detect any flaw that might exist in the piping 1 which has a protuberance, such as a branch pipe 1a. In this embodiment, when inspection of the piping 1 is performed by effecting scanning of the probe 4, the traveling member 2 which is traveling is stopped when it reaches a point immediately in front of the branch pipe 1a, and then inspection of almost all portions of the outer peripheral surface of the piping 1 that remain to be inspected can be performed, excepting the branch pipe 1a, by scanning the probe 4 by expanding and contracting the retractile arm 23 as the turning member 3 is caused to turn about the traveling member 2 which remains stationary.

From the foregoing description, it will be appreciated that the ultrasonic flaw detector driving apparatus according to the invention offers the following advantages which ultrasonic flaw detector driving apparatus of the prior art having a guide rail are unable to offer:

(1) Since the ultrasonic flaw detector driving apparatus according to the invention is of a type having no guide rail which travels directly on the piping, it is possible to continuously scan the ultrasonic wave probe along the whole length of elongated piping. Combined with the ease with which the apparatus can be mounted to and dismounted from an outer peripheral surface of the piping, this can reduce the time required for inspection of the piping greatly.

(2) The ultrasonic flaw detector driving apparatus according to the invention can be moved on a portion of the outer peripheral surface of the piping which is located in a narrow area in the inspection site to which no access can be applied. This is conducive to an increase in the area of the zone in which inspection procedure can be performed; and (3) The invention enables an overall compact size and a light weight to be obtained in a ultrasonic flaw detector driving apparatus.

What is claimed is:

1. An ultrasonic flaw detector driving apparatus of a type having no guide rail and enabling inspection of piping to be achieved, comprising:

a traveling member capable of being removably mounted on an outer peripheral surface of the piping; and a turning member detachably mounted to an outer peripheral surface of the traveling member;

wherein the traveling member is equipped with a multiplicity of sets of traveling rolling elements located in position on an outer peripheral surface of the piping spaced apart from one another circumferentially of the piping while each set of traveling rolling elements comprises at least two rolling elements which are in contact with the outer peripheral surface of the piping and spaced apart from each other axially of the piping so that as the traveling rolling elements are rotated the traveling member can travel axially of the piping on the outer peripheral surface thereof, and wherein the turning member is equipped with at least one ultrasonic wave probe for effecting scanning to perform inspection of the piping and capable of turning about the traveling member circumferentially of the piping.

2. An ultrasonic flaw detector driving apparatus of a type having no guide rail as claimed in claim 1, wherein the traveling member is further equipped with drive means for causing the traveling rolling elements to rotate, and drive means for causing the turning member to move in turning movement about said traveling member circumferentially of the pipe.

3. An ultrasonic flaw detector driving apparatus of a type having no guide rail type as claimed in claim 2, wherein the drive means for causing the traveling rolling elements to rotate comprises a traveling member drive motor and gear means for transmitting motive force from the drive motor to the traveling rolling elements, and wherein the drive means for causing the turning member to move in turning movement comprises a turning member drive motor and gear means for transmitting motive force from the drive motor to an internal gear fitted to the turning member.

4. An ultrasonic flaw detector driving apparatus as claimed in claim 1, wherein at least one set of traveling rolling elements of the multiplicity of sets of traveling rolling elements spaced apart from one another circumferentially of traveling member is pivotably connected to the traveling member and movable between a closed position in which the rolling elements of the set spaced apart from each other axially of the traveling member are located on the traveling member and an open position in which the rolling elements of the set are away from the traveling member transversely thereof to allow the traveling member to be mounted to and removed from the piping from the side.

5. An ultrasonic flaw detector driving apparatus of a type having no guide rail as claimed in claim 2, wherein component parts of the traveling member including the drive means for causing the traveling rolling elements to rotate and the drive means for causing the turning member to move in turning movement are arranged in scattered relationship in such a manner that the traveling member is balanced in weight peripherally thereof.

6. An ultrasonic flaw detector driving apparatus of a type having no guide rail as claimed in claim 1, wherein the traveling rolling elements comprise rollers.

7. An ultrasonic flaw detector driving apparatus of a type having no guide rail as claimed in claim 6, wherein the traveling rollers comprise a multiplicity of sets of rollers each set consisting of two rollers arranged at a caster angle.

8. An ultrasonic flaw detector driving apparatus of a type having no guide rail as claimed in claim 1, wherein the traveling rolling elements comprise crawlers.

9. An ultrasonic flaw detector driving apparatus of a type having no guide rail as claimed in claim 1, wherein the ultrasonic wave probe is connected to one end face of the turning member through a retractile arm member capable of expansion and contraction lengthwise of the piping.

* * * * *